United States Patent
Lee et al.

(10) Patent No.: US 12,297,482 B2
(45) Date of Patent: May 13, 2025

(54) RAPID CELL CULTURE TEST DEVICE DESIGNED SUCH THAT FLUID FILMS WITH UNIFORM THICKNESS ARE FORMED

(71) Applicant: QuantaMatrix Inc., Seoul (KR)

(72) Inventors: Gi Yoon Lee, Seoul (KR); Tae Geun Lim, Seoul (KR); Dong Young Kim, Seongnam-si (KR)

(73) Assignee: QUANTAMATRIX INC., Seoul (KR)

( * ) Notice: Subject to any disclaimer, the term of this patent is extended or adjusted under 35 U.S.C. 154(b) by 573 days.

(21) Appl. No.: 17/760,740

(22) PCT Filed: Oct. 6, 2020

(86) PCT No.: PCT/KR2020/013590
§ 371 (c)(1),
(2) Date: Mar. 15, 2022

(87) PCT Pub. No.: WO2021/187703
PCT Pub. Date: Sep. 23, 2021

(65) Prior Publication Data
US 2022/0348979 A1  Nov. 3, 2022

(30) Foreign Application Priority Data
Mar. 16, 2020 (KR) .......... 10-2020-0032132

(51) Int. Cl.
*C12Q 1/20* (2006.01)
*B01L 3/00* (2006.01)

(52) U.S. Cl.
CPC .......... *C12Q 1/20* (2013.01); *B01L 3/50853* (2013.01); *B01L 2200/16* (2013.01); *B01L 2300/044* (2013.01); *B01L 2300/0829* (2013.01); *B01L 2300/0851* (2013.01)

(58) Field of Classification Search
None
See application file for complete search history.

(56) References Cited

U.S. PATENT DOCUMENTS

2005/0173059 A1   8/2005   Ringleben et al.

FOREIGN PATENT DOCUMENTS

| | | | |
|---|---|---|---|
| EP | 3434370 A1 * | 1/2019 | ............... B01L 3/00 |
| JP | 2015029431 A | 2/2015 | |
| JP | 2018009936 A | 1/2018 | |
| JP | 2019170289 A | 10/2019 | |
| KR | 101377694 B1 | 3/2014 | |
| KR | 101443074 B1 | 9/2014 | |
| KR | 101446526 B1 | 10/2014 | |
| KR | 20160147240 A | 12/2016 | |
| KR | 101711105 B1 | 3/2017 | |
| KR | 102029142 B1 | 10/2019 | |

OTHER PUBLICATIONS

International Search report of PCT/KR2020/013590, Jan. 15, 2021, English translation.

* cited by examiner

*Primary Examiner* — Michelle F. Paguio Frising
(74) *Attorney, Agent, or Firm* — STIP Law Group, LLC

(57) ABSTRACT

Provided is a multi-well-based rapid cell culture test device designed such that fluid films with a uniform thickness are formed. The rapid cell culture test device has an array structure of a plurality of aligned well units, each of which includes a first sub-well in which a first fluid is accommodated and a barrier structure surrounding the first sub-well to define the area of the first sub-well. A capillary channel recessed from the bottom surface of the first sub-well while traversing the bottom surface is formed to accommodate the first fluid and the barrier structure is divided into a barrier portion A located adjacent to one end of the capillary channel and a barrier portion B located adjacent to the other end of the capillary channel.

12 Claims, 12 Drawing Sheets

[FIG. 1]
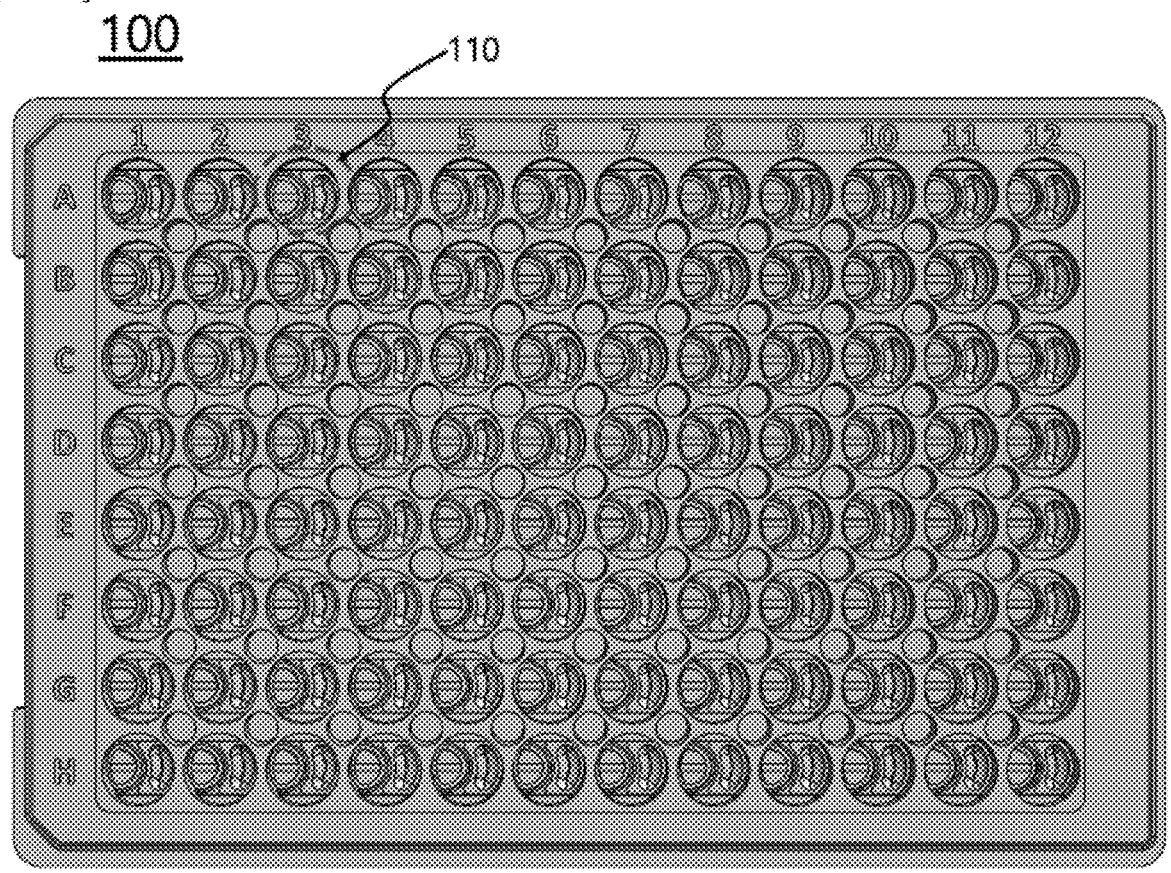

[FIG. 2A]
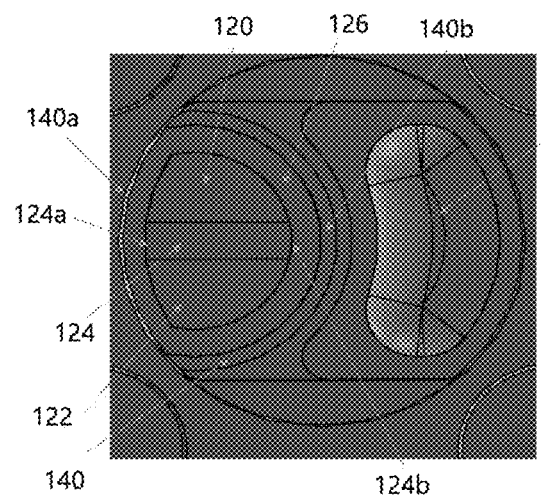
[FIG. 2B]
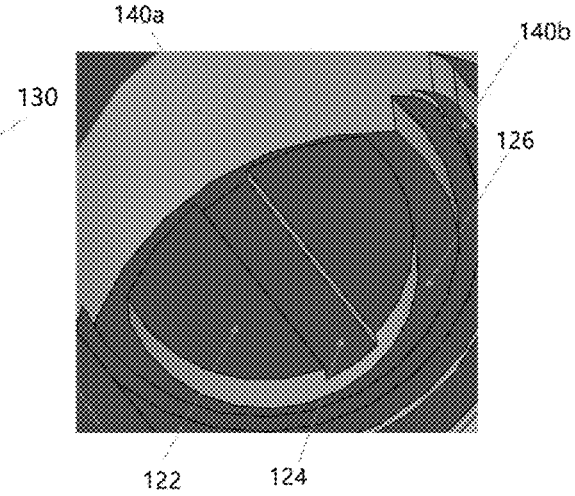
[FIG. 2C]
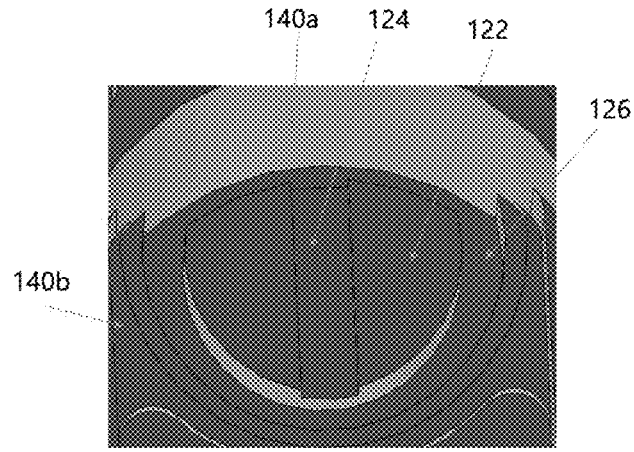
[FIG. 2D]
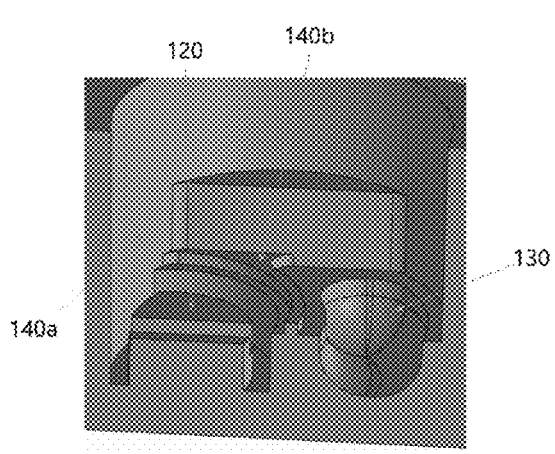

[FIG. 3A]
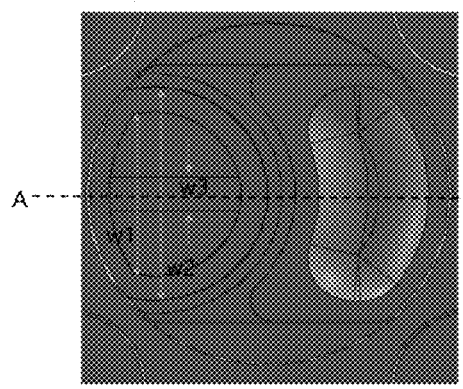
[FIG. 3B]
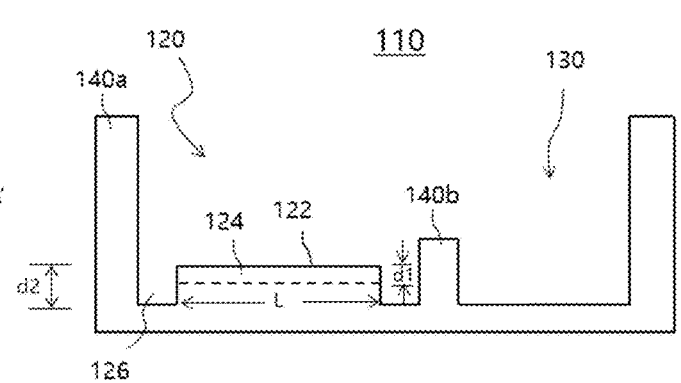
[FIG. 3C]
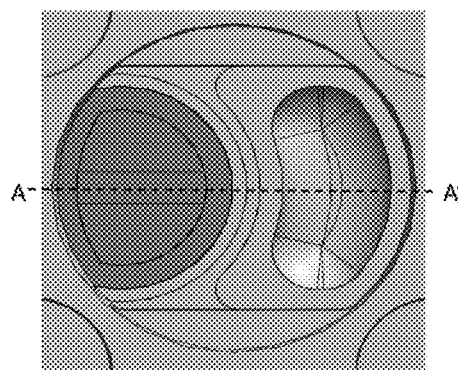
[FIG. 3D]
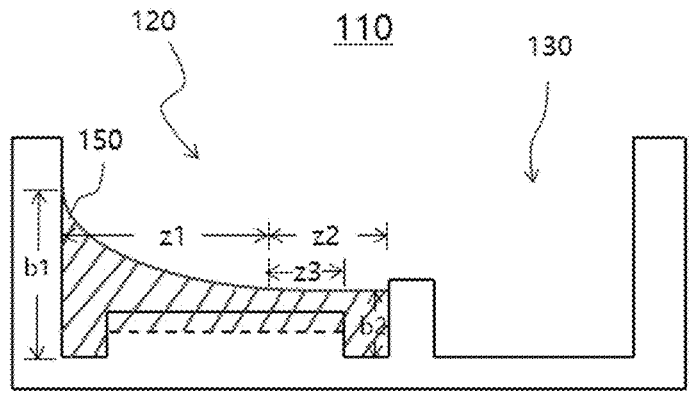

[FIG. 4A]
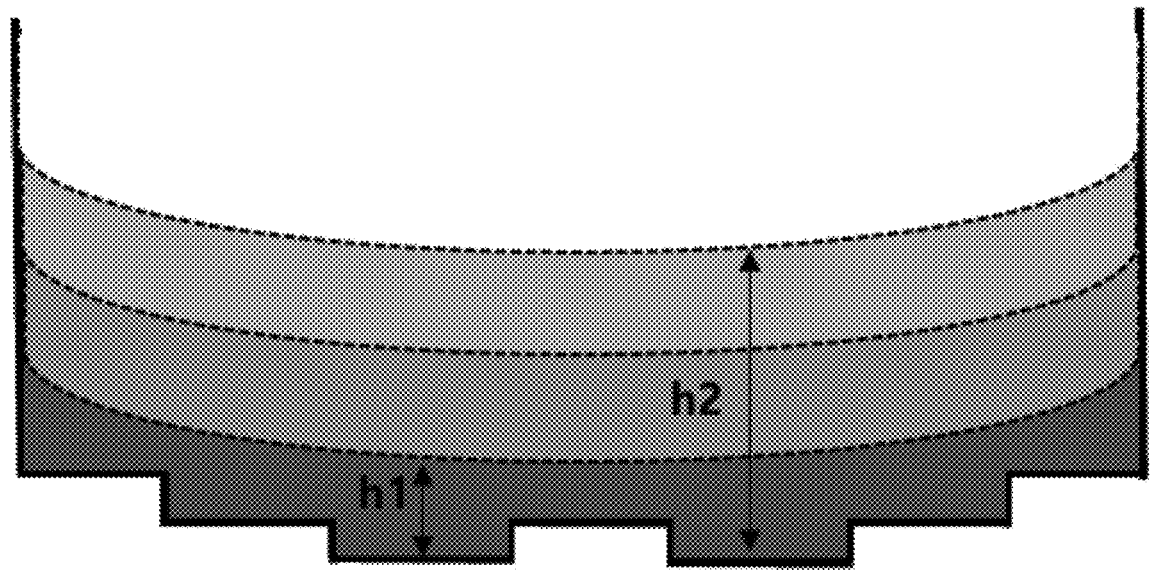
[FIG. 4B]
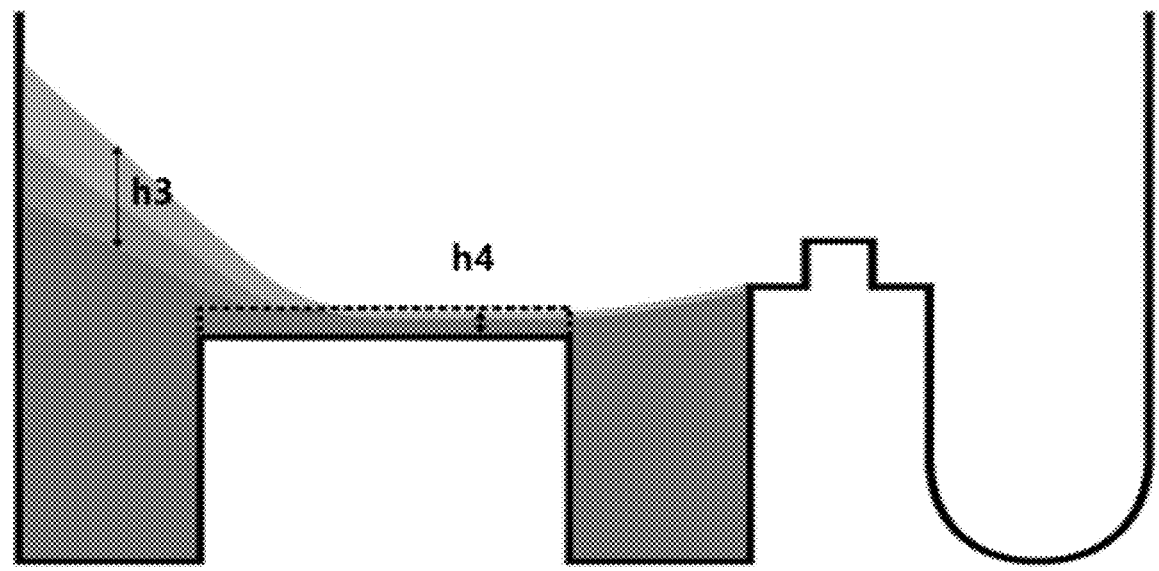

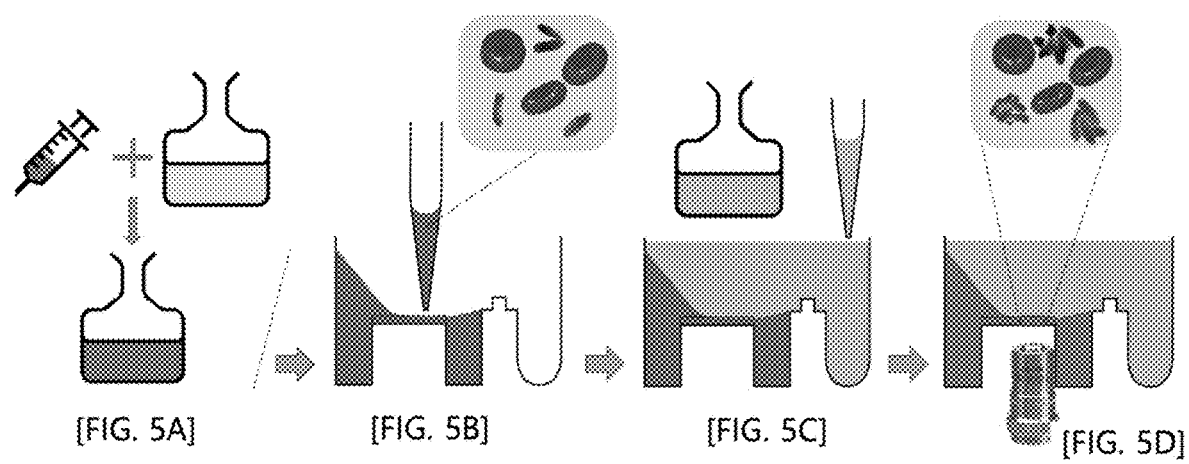
[FIG. 5A]  [FIG. 5B]  [FIG. 5C]  [FIG. 5D]
[FIG. 6]
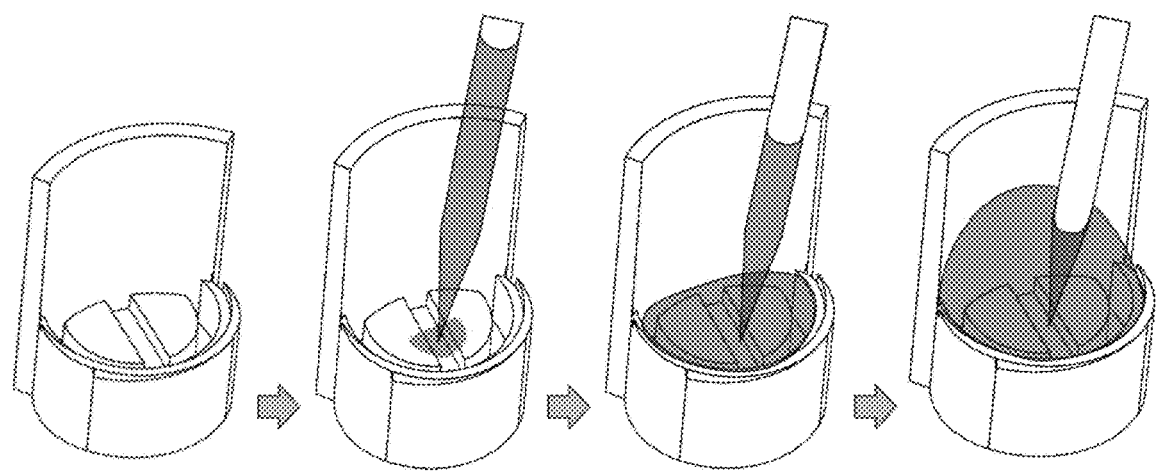

[FIG. 7]
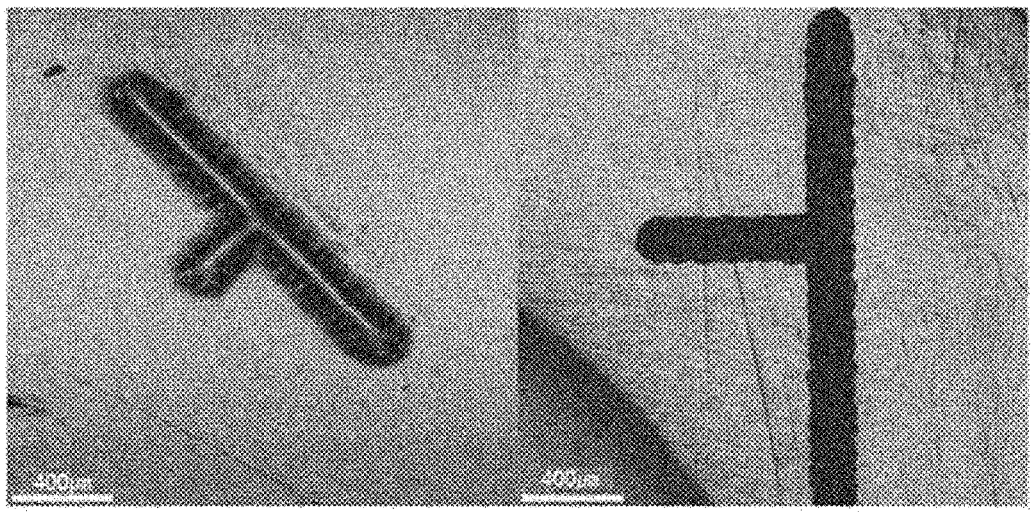
[FIG. 8]
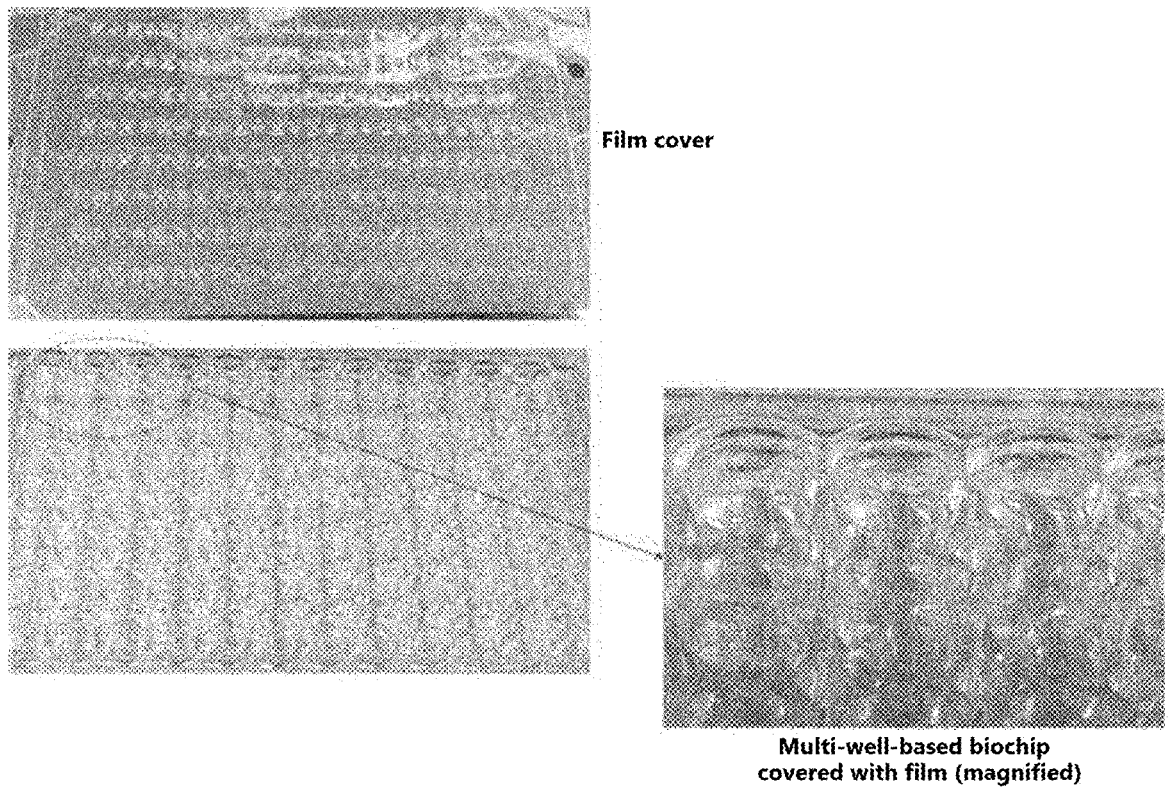

[FIG. 9A]
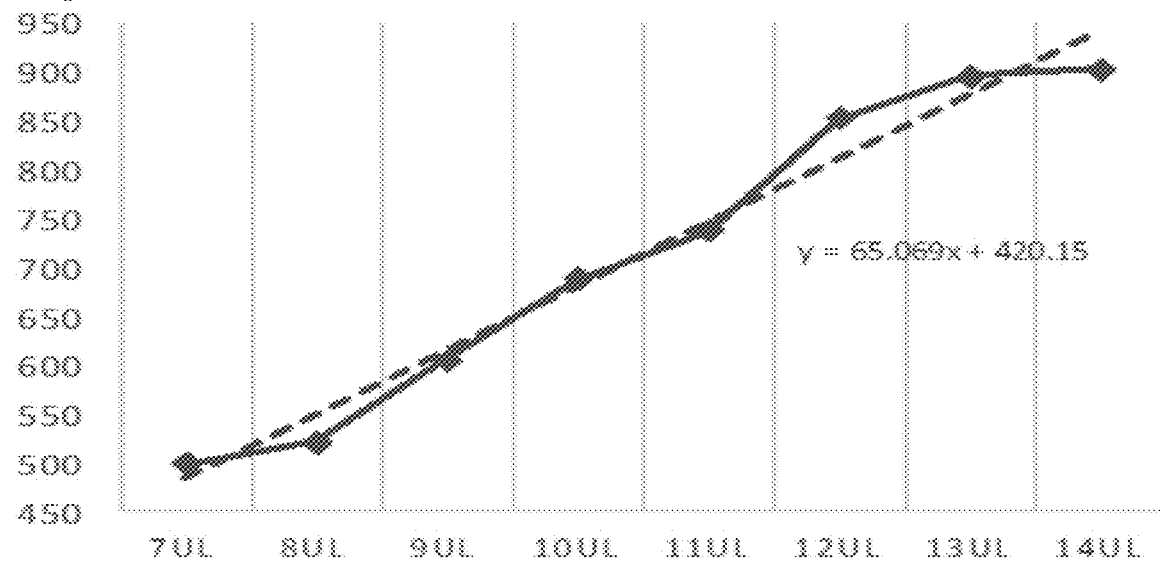
[FIG. 9B]
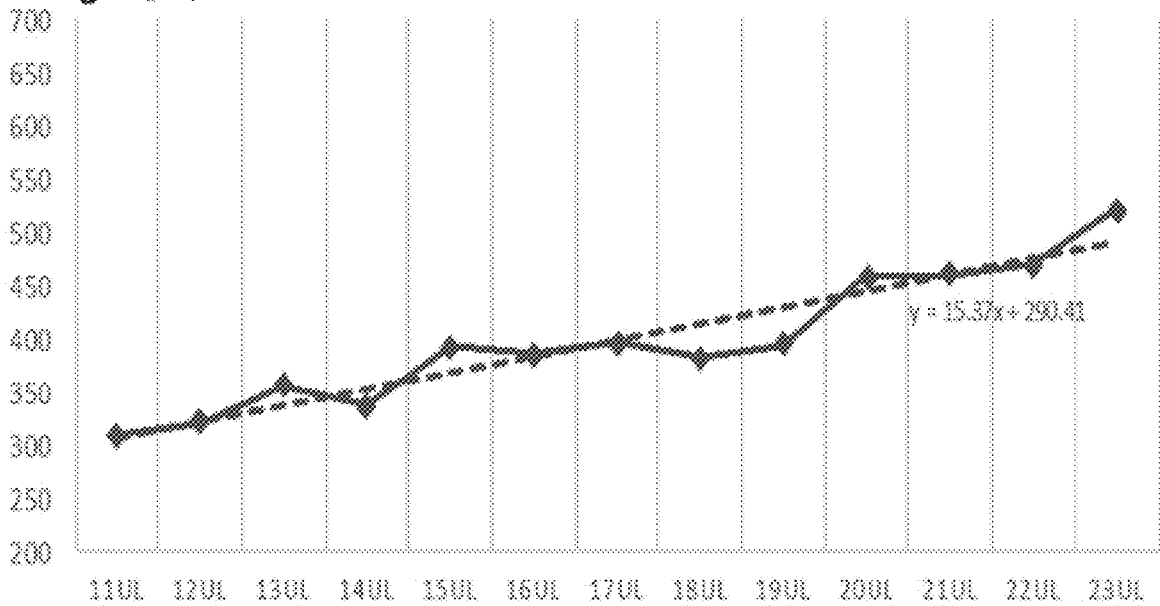

[FIG. 10]
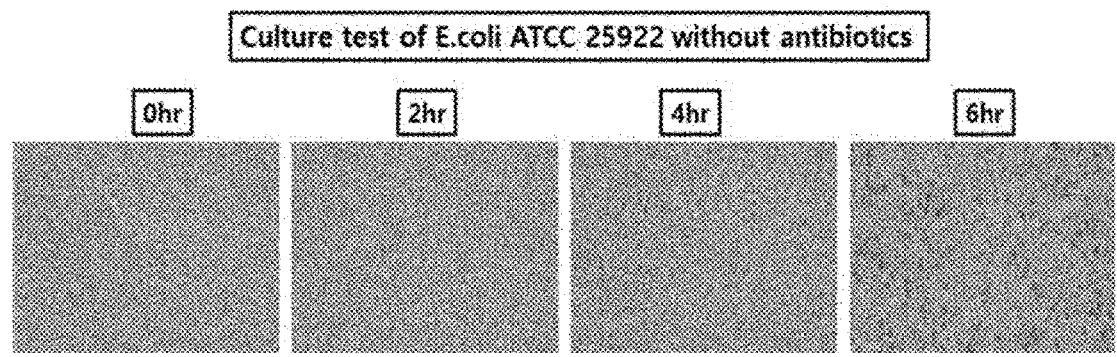
[FIG. 11]
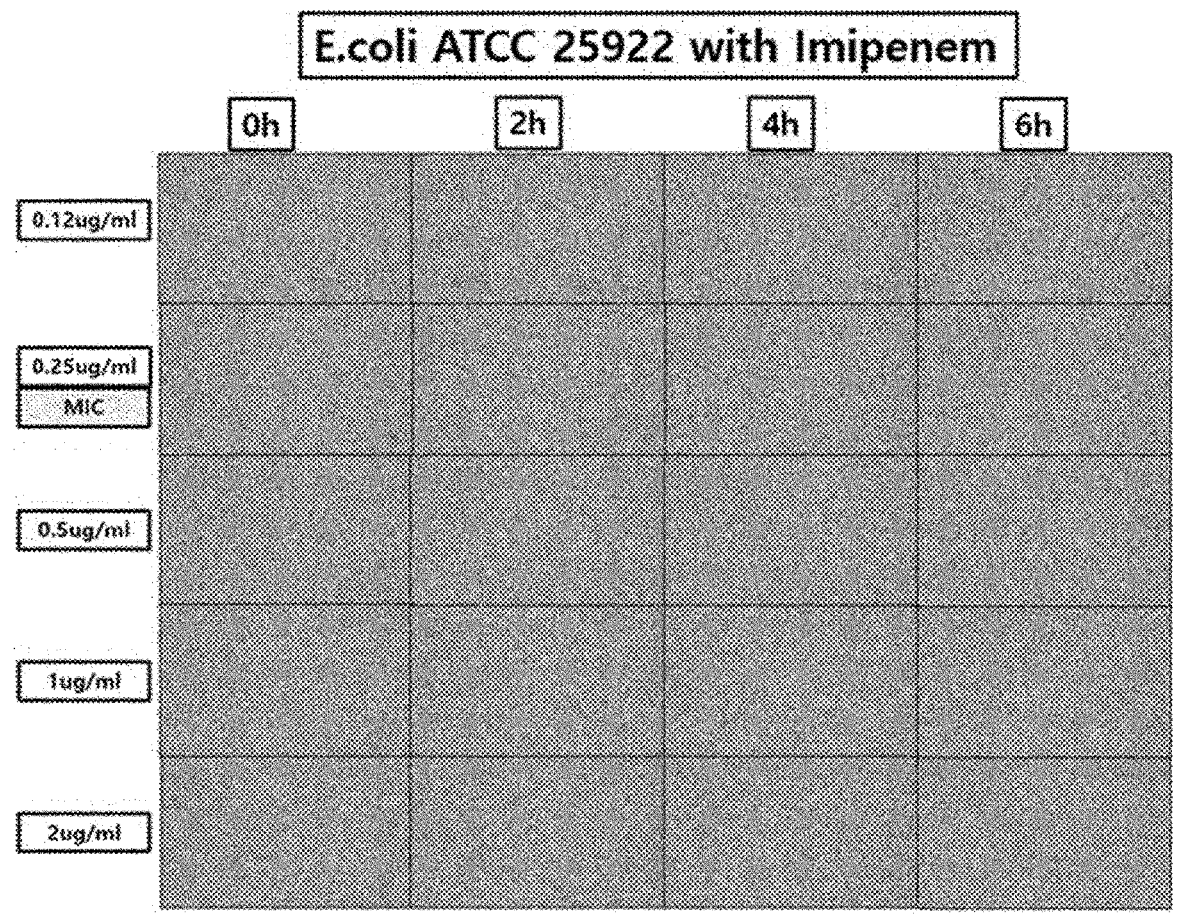

[FIG. 12]
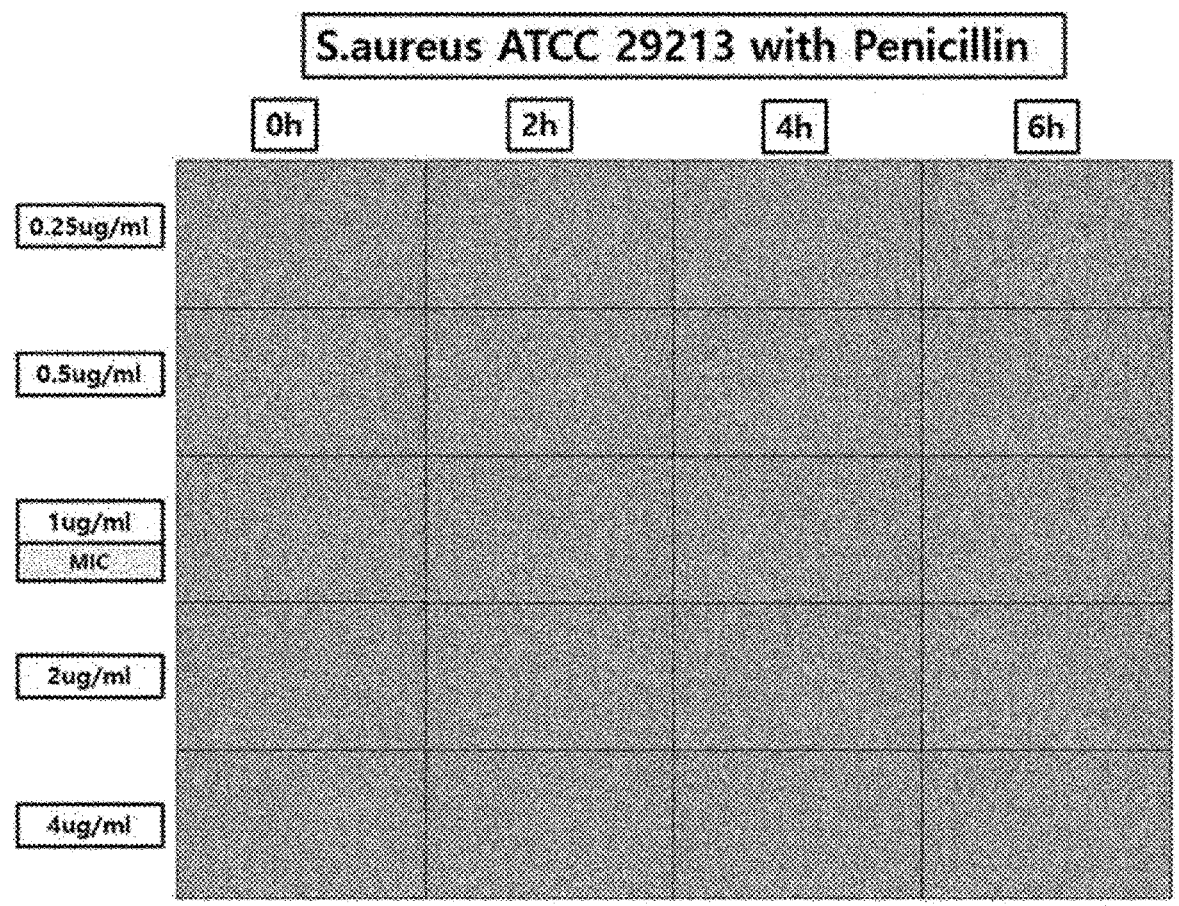

[FIG. 13]
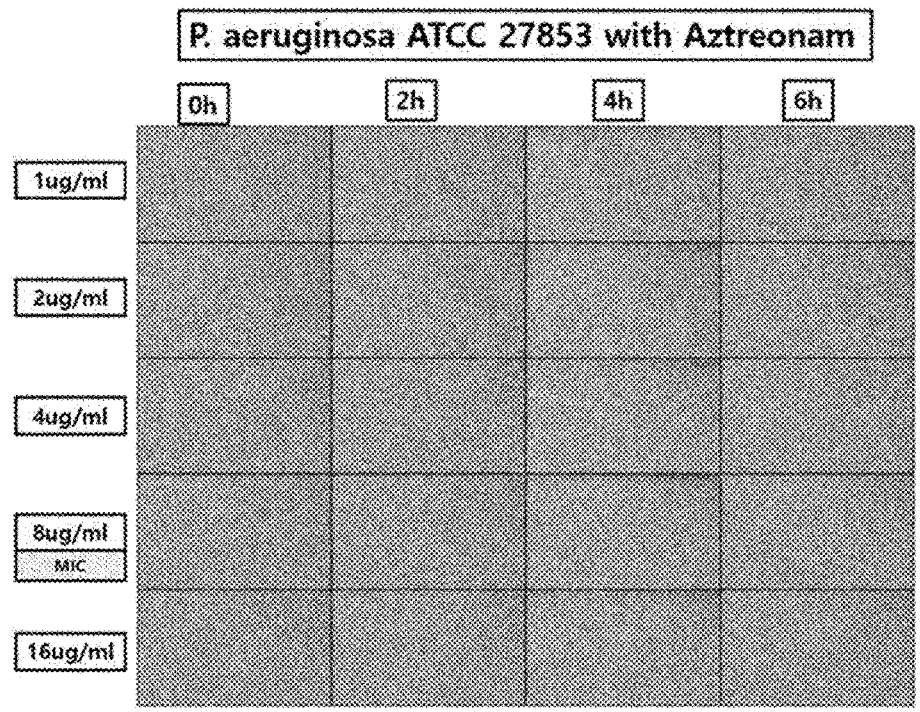
[FIG. 14]
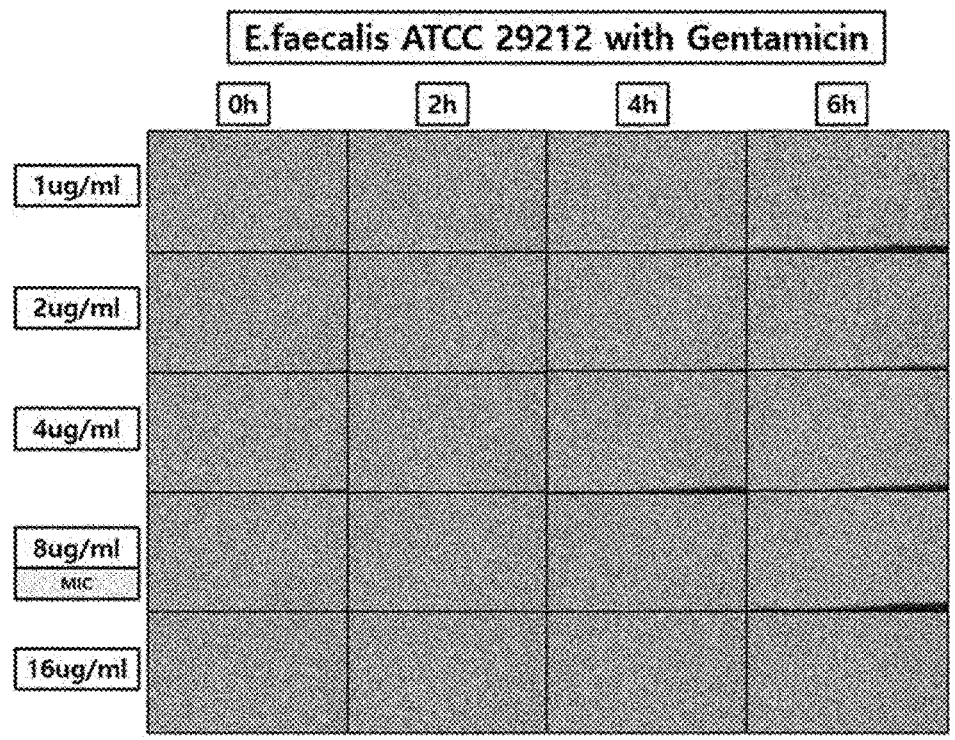

[FIG. 15]

| | Gram Negative | | | DRAST | BMD | DRAST | BMD | DRAST | BMD | DRAST | BMD |
|---|---|---|---|---|---|---|---|---|---|---|---|
| 항생제 | Enterobacteriaceae | Pseudomonas aeruginosa | Acinetobacter | E.cloacae | | K.pneumoniae | | P.aeruginosa | | A.baumannii | |
| Amikacin | 16, 64 | 16, 64 | 16, 64 | <=8(S) | <=4(S) | >=64(R) | >=32(R) | <=8(S) | <=4(S) | <=8(S) | <=4(S) |
| Amoxicillin/Clavulanate | 8/4, 32/16 | - | - | >32/16(R) | >16/8(R) | >32/16(R) | >16/8(R) | - | - | - | - |
| Ampicillin | 8, 32 | - | - | >32(R) | >32(R) | - | - | - | - | - | - |
| Ampicillin/Sulbactam | 8/4, 32/16 | - | 8/4, 32/16 | >32/16(R) | >32/16(R) | >32/16(R) | >32/16(R) | - | - | <=8/4(S) | <=8/4(S) |
| Aztreonam | 4, 16 | 8, 32 | - | >32(R) | >32(R) | >32(R) | >32(R) | 8(S) | 4(S) | - | - |
| Cefazolin | 2, 8 | - | - | >32(R) | >32(R) | >32(R) | >32(R) | - | - | - | - |
| Cefepime | 2, 16 | 8, 32 | 8, 32 | >32(R) | 16(I) | >32(R) | >32(R) | 4(S) | 2(S) | <=1(S) | <=2(S) |
| Cefotaxime | 1, 4 | - | - | >32(R) | >64(R) | >32(R) | >64(R) | - | - | 4(S) | 8(S) |
| Ceftazidime | 4, 16 | 8, 32 | 8, 32 | >32(R) | >32(R) | >32(R) | >32(R) | 4(S) | 2(S) | 2(S) | <=1(S) |
| Ciprofloxacin | 0.05, 1 | 1, 4 | 1, 4 | 1(S) | 2(I) | >4(R) | >4(R) | 0.12(S) | 0.12(S) | <=0.06(S) | <=1(S) |
| Colistin | 2, 4 | 2, 4 | 2, 4 | - | - | - | - | <=2(S) | <=0.5(S) | <=2(S) | <=2(S) |
| Ertapenem | 0.5, 2 | - | - | 1(S) | >2(R) | >=2(R) | >=2(R) | - | - | - | - |
| Gentamicin | 4, 16 | 4, 16 | 4, 16 | 4(S) | 4(S) | >16(R) | >16(R) | <=2(S) | <=2(S) | <=4(S) | <=4(S) |
| Imipenem | 1, 4 | 2, 8 | 2, 8 | <=1(S) | <=0.5(S) | >16(R) | >16(R) | 2(S) | 1(S) | <=1(S) | <=1(S) |
| Meropenem | 1, 4 | 2, 8 | 2, 8 | <=1(S) | <=1(S) | >16(R) | >16(R) | <=1(S) | <=1(S) | <=1(S) | <=1(S) |
| Minocycline | 4, 8 | - | 4, 16 | - | - | - | - | - | - | <=4(S) | <=4(S) |
| Piperacillin/Tazobactam | 16/4, 128/4 | 16/4, 128/4 | 16/4, 128/4 | >128/4(R) | >=128/4(R) | >128/4(R) | >=128/4(R) | <=8/4(S) | <=4/4(S) | <=8/4(S) | <=16/4(S) |
| Trimethoprim/Sulfamethoxazole | 2/38, 4/76 | - | 2/38, 4/76 | >=8/152(R) | 8/152(R) | >=8/152(R) | >=4/76(R) | - | - | <=2/38(S) | <=2/38(S) |

[FIG. 16]

| | Gram Positive | | DRAST | BMD | DRAST | BMD | DRAST | BMD | DRAST | BMD |
|---|---|---|---|---|---|---|---|---|---|---|
| | Staphylococcus | Enterococcus | S.aureus | S.aureus | S.epidermidis | S.epidermidis | E.faecalis | E.faecalis | E.faecium | E.faecium |
| 항생제 | | | | | | | | | | |
| Ampicillin | - | 8, 16 | - | - | - | - | 8(S) | 0.25(S) | >=16(R) | >=16(R) |
| Ciprofloxacin | 1, 4 | - | <=1(S) | <=1(S) | <=1(S) | <=1(S) | | | | |
| Clindamycin | 0.5, 4 | - | <=0.25(S) | <=0.25(S) | <=0.25(S) | <=0.25(S) | | | | |
| Erythromycin | 0.5, 8 | 0.5, 8 | <=0.5(S) | <=0.5(S) | <=0.5(S) | <=0.5(S) | | | | |
| Gentamicin | 4, 16 | - | >=16(R) | >=16(R) | >=16(R) | >=16(R) | | | | |
| Levofloxacin | 1, 4 | 2, 8 | <=1(S) | <=1(S) | <=1(S) | <=1(S) | | | | |
| Linezolid | 4, 8 | 2, 8 | <=2(S) | <=2(S) | <=2(S) | 1(S) | <=2(S) | 2(S) | 4(I) | 8(R) |
| Oxacillin | 2, 4 (0.25, 0.5) | - | >=4(R) | >2(R) | 1(R) | 1(R) | | | | |
| Penicillin | 0.12, 0.25 | 8, 16 | >=16(R) | >=16(R) | 0.25 | 0.25 | >=16(R) | >8(R) | >=16(R) | >=16(R) |
| Rifampicin | 1, 4 | 1, 4 | <=0.06(S) | <=0.06(S) | <=0.06(S) | <=0.06(S) | | | | |
| Tetracycline | 4, 16 | 4, 16 | <=1(S) | <=1(S) | <=1(S) | 2(S) | | | | |
| Trimethoprim/Sulfamethoxazole | 2/38, 4/76 | - | <=2/38(S) | <=0.5/9.5(S) | <=2/38(S) | <=0.5/9.5(S) | | | | |
| Vancomycin | 2, 16 | 4, 32 | <=2(S) | <=2(S) | <=2(S) | 4(S) | <=2(S) | <=2(S) | <=32(R) | <=32(R) |
| Gentamicin High-Level | - | 500 | - | - | - | - | 500(S) | 500(S) | 500(R) | >500(R) |
| Streptomycin High-Level | - | 1,000 | - | - | - | - | <=512(S) | <=1000(S) | <=512(S) | <=512(S) |

RAPID CELL CULTURE TEST DEVICE DESIGNED SUCH THAT FLUID FILMS WITH UNIFORM THICKNESS ARE FORMED

CROSS-REFERENCE TO RELATED APPLICATIONS

This application is the U.S. National Phase under 35 U.S.C. § 371 of International Application No. PCT/KR2020/013590 filed on Oct. 6, 2020, which in turn claims the benefit of Korean Application No. 10-2020-0032132 filed on Mar. 16, 2020, the disclosures of which are incorporated by reference into the present application.

TECHNICAL FIELD

The present disclosure relates generally to a rapid cell culture test device designed such that fluid films with a uniform thickness are formed.

BACKGROUND ART

Generally, antibiotic susceptibility testing (response of bacteria to a drug) is performed by placing bacteria in a multi-well plate, introducing a drug in a liquid form, and monitoring time-dependent changes of the bacteria using an optical measurement system. According to the Kirby-Bauer (KB) method for antibiotic susceptibility testing, bacteria are inoculated into a solid medium, placing antibiotic-absorbed papers thereon, and observing bacterial growth. In the case of microdilution testing in liquid media, a number of automated systems such as VITEK2, Microscan, and Phoenix have been developed for antibiotic susceptibility testing. Such a system can be used for antibiotic susceptibility testing by placing an antibiotic in millimeter-sized wells, introducing bacteria and a liquid medium into the wells, and statistically monitoring and determining the bacterial growth based on turbidity.

Such methods for testing the responses of bacteria to drugs require a long incubation time (usually 16-24 hours) for cell growth above a predetermined level (usually one million cells per ml) because the degrees of bacterial growth are determined by turbidity (absorbance) measurements. In contrast, a system for observing the growth of colonies of bacteria embedded in gelled agarose at fixed locations requires as short as 2 hours, usually 6 hours to obtain drug test results. Therefore, this system is expected to make a great contribution to the diagnosis and treatment of bacteremia and subsequent life-threatening sepsis.

In such a system, a medium surrounding a specified amount of the agarose and an antibiotic component penetrate into the agarose and affect the growth of the bacteria. The degree of penetration is dependent on the bacterial species and the antibiotic type. Thus, when the agarose is thick, the height can determine a difference in the degree of growth.

Since optical measurement areas for observation of the bacterial growth are fixed, control over the volumes of the agarose and the medium dispensed in the automated system is required to ensure a constant distance from the interface between the agarose and the medium. However, a considerable cost is inevitably involved in designing the system such that the agarose having a viscosity at around its gelling point is quantitatively dispensed at a CV of less than 10%.

Thus, there is a need to design a chip such that variations in distance from imaging areas to agarose-medium interfaces are minimized despite deviations in the amounts of the agarose and medium dispensed above predetermined levels.

DETAILED DESCRIPTION OF THE INVENTION

Problems to be Solved by the Invention

The present disclosure has been made in an effort to solve the above-described problems and intends to provide a rapid cell culture test device designed such that fluid films with a uniform thickness are formed.

Means for Solving the Problems

One aspect of the present disclosure provides a multi-well-based rapid cell culture test device designed such that fluid films with a uniform thickness are formed and having an array structure of a plurality of aligned well units, each of which includes a first sub-well in which a first fluid is accommodated and a barrier structure surrounding the first sub-well to define the area of the first sub-well wherein a capillary channel recessed from the bottom surface of the first sub-well while traversing the bottom surface is formed to accommodate the first fluid and the barrier structure is divided into a barrier portion A located adjacent to one end of the capillary channel and a barrier portion B located adjacent to the other end of the capillary channel, the barrier portion A being greater in height than the barrier portion B such that when the barrier portion A is wetted with the first fluid introduced into the first sub-well along its inner wall, a change in the level of the first fluid at the other end of the capillary channel depending on the amount of the first fluid dispensed is minimized.

According to one embodiment, the cell culture test device may further include microchannels, each of which is formed surrounding the corresponding bottom surface along the circumference of the inner wall of the barrier structure to allow the introduced first fluid to uniformly fill the first sub-well.

According to one embodiment, the inner wall of the barrier portion A may be hydrophilized.

According to one embodiment, the barrier portion A located adjacent to one end of the capillary channel may include an edge of the inner wall of the first sub-well.

According to one embodiment, the microchannel may be recessed deeper than the capillary channel recessed from the bottom surface.

According to one embodiment, at least a portion of the bottom surface may be made of an optically transparent material such that targets present in the first fluid are observable through the bottom surface.

According to one embodiment, the cell culture test device may further include second sub-wells spatially separated from the first sub-wells to accommodate a second fluid and designed to load a bioactive agent in a solid form at specific locations thereof.

According to one embodiment, the first fluid may be a mixture solution of a gelling agent-containing liquid medium and a biological agent, and a second fluid may be a solution containing a bioactive agent or may include a solvent capable of dissolving a bioactive agent in a solid form.

According to one embodiment, the multi-well-based cell culture test device may include polyethylene (PE), polypropylene (PP), polymethyl methacrylate (PMMA), cyclic olefin polymer (COP), polystyrene (PS), polycarbonate (PC), Teflon™, polyvinyl chloride (PVC), polybutylene terephthalate (PBT), polyethylene terephthalate (PET) or acrylonitrile-butadiene-styrene copolymer (ABS) and may be provided with a cover film made of silicone, polyethylene terephthalate (PET), polyethylene (PE), polypropylene (PP), polystyrene (PS), polycarbonate (PC), Teflon™ or polyvinyl chloride (PVC).

According to one embodiment, the cover film may have cruciform or X-shaped punches formed at positions corresponding to the sub-wells of the well units constituting the multi-well-based cell culture test device and serving as inlets through which the first fluid is introduced and inlets through which a second fluid is introduced.

A further aspect of the present disclosure provides a cell analysis method using a multi-well-based cell culture test device having an array structure of a plurality of aligned well units, each of which includes a first sub-well in which a first fluid is accommodated and a barrier structure surrounding the first sub-well to define the area of the first sub-well wherein a capillary channel recessed from the bottom surface of the first sub-well while traversing the bottom surface is formed to accommodate the first fluid and the barrier structure is divided into a barrier portion A located adjacent to one end of the capillary channel and a barrier portion B located adjacent to the other end of the capillary channel, the barrier portion A being greater in height than the barrier portion B such that when the barrier portion A is wetted with the first fluid introduced into the first sub-well along its inner wall, a change in the level of the first fluid at the other end of the capillary channel depending on the amount of the first fluid dispensed is minimized, the method including (a) providing a mixture solution of a gelling agent-containing liquid medium and a biological agent to the capillary channel recessed from the bottom surface of the first sub-well, (b) gelling the mixture solution to form a solid thin film that is immobilized with the biological agent and minimizes elevation of the liquid-gas interface, (c) providing a solution containing a bioactive agent to a second sub-well or providing a solvent capable of dissolving a bioactive agent in a solid form to a second sub-well loaded with the bioactive agent, (d) introducing the bioactive agent-containing solution or the solvent capable of dissolving the bioactive agent in such an amount that the solution or the solvent crosses over the barrier, to allow the bioactive agent to diffuse into the solid thin film in the first sub-well, and (e) observing responses of the biological agent to the bioactive agent.

According to one embodiment, the method may further include (f) observing changes of the biological agent responding to the bioactive agent on a single cell colony basis to determine the minimum inhibitory concentration (MIC) or minimum biofilm eradication concentration (MBEC) of the bioactive agent.

Effects of the Invention

The rapid cell culture test device of the present disclosure is designed such that fluid films with a uniform thickness are formed. Due to this design, the height of solid thin films as the fluid films can be maintained constant, allowing for accurate testing compared to conventional antibiotic test devices. The cell culture test device of the present disclosure uses cells immobilized in the solid thin films to observe the behavior of an antibiotic, enabling rapid antibiotic susceptibility testing compared to conventional devices.

In addition, the rapid cell culture test device of the present disclosure can generally observe changes in the growth of single bacteria within several tens of minutes (usually 30 minutes) and changes in the growth of single colonies of bacteria within 4 to 6 hours. Accordingly, the rapid cell culture test device of the present disclosure can more accurately and rapidly determine the effects of a bioactive agent on a biological agent than conventional devices.

Furthermore, the rapid cell culture test device of the present disclosure can observe changes of a biological agent responding to a bioactive agent on a single cell colony basis to determine the minimum inhibitory concentration (MIC) or minimum biofilm eradication concentration (MBEC) of the bioactive agent, thus being very useful for biofilm assay as well as antibiotic susceptibility testing.

BRIEF DESCRIPTION OF THE DRAWINGS

FIG. 1 illustrates a rapid cell culture test device designed such that fluid films with a uniform thickness are formed according to one embodiment of the present disclosure.

FIG. 2 schematically illustrates a well unit structure of a rapid cell culture test device designed such that fluid films with a uniform thickness are formed according to one embodiment of the present disclosure, when viewed in different directions.

FIG. 3 illustrates views for explaining the role, function, and effect of a barrier structure in a rapid cell culture test device according to one embodiment of the present disclosure depending on the shape of the barrier structure.

FIG. 4 illustrates cross-sectional views comparing different levels of a fluid introduced into (a) a well unit having a general well structure and (b) a well unit of a cell culture test device according to one embodiment of the present disclosure.

FIG. 5 shows an antibiotic testing process using a cell culture test device according to one embodiment of the present disclosure.

FIG. 6 shows loading of a sample into a first sub-well of a cell culture test device according to one embodiment of the present disclosure.

FIG. 7 shows focus marks provided on the undersides of first sub-wells of a cell culture test device according to one embodiment of the present disclosure.

FIG. 8 shows a rapid cell culture test device designed such that fluid films with a uniform thickness are formed according to one embodiment of the present disclosure, which is provided with a cover film.

FIG. 9 shows the heights of solid thin films formed in imaging areas by introducing different amounts of a fluid into (a) well units having a general well structure and (b) well units of a cell culture test device according to one embodiment of the present disclosure.

FIG. 10 shows the growth of reference strain E. coli ATCC 25922 without antibiotics, which was observed at regular time intervals using a cell culture test device according to one embodiment of the present disclosure.

FIG. 11 shows a process for susceptibility testing of reference strain E. coli ATCC 25922 to imipenem as an antibiotic, which was observed at regular time intervals using a cell culture test device according to one embodiment of the present disclosure.

FIG. 12 shows a process for susceptibility testing of reference strain S. aureus ATCC 29213 to penicillin as an antibiotic, which was observed at regular time intervals using a cell culture test device according to one embodiment of the present disclosure.

FIG. 13 shows a process for susceptibility testing of reference strain P. aeruginosa ATCC 27853 to aztreonam as an antibiotic, which was observed at regular time intervals using a cell culture test device according to one embodiment of the present disclosure.

FIG. 14 shows a process for susceptibility testing of reference strain *E. faecalis* ATCC 29212 to gentamicin as an antibiotic, which was observed at regular time intervals using a cell culture test device according to one embodiment of the present disclosure.

FIG. 15 shows the results of susceptibility testing of Gram-negative strains *Enterobacter cloacae, Klebsiella pneumoniae, Pseudomonas aeruginosa*, and *Acinetobacter baumannii* obtained from four blood samples to antibiotics, which was observed using a cell culture test device according to one embodiment of the present disclosure.

FIG. 16 shows the results of susceptibility testing of Gram-positive strains *Staphylococcus aureus, Staphylococcus epidermidis, Enterococcus faecalis*, and *Enterococcus faecium* obtained from four blood samples to antibiotics, which was observed using a cell culture test device according to one embodiment of the present disclosure.

MODE FOR CARRYING OUT THE INVENTION

Embodiments of the present disclosure will now be described in detail with reference to the accompanying drawings.

However, the present disclosure may be embodied in many different forms and should not be construed as limited to the embodiments set forth herein. Rather, these embodiments are provided so that this disclosure will be thorough and complete, and will fully convey the scope of the present disclosure to those skilled in the art. In the drawings, the dimensions, such as widths and thicknesses, of elements may be exaggerated for clarity. The drawings are explained from an observer's point of view. It will be understood that when an element is referred to as being "on" another element, it can be directly on the other element, or one or more intervening elements may also be present therebetween. Those skilled in the art will appreciate that many modifications can be made without departing from the spirit of the disclosure. Throughout the accompanying drawings, the same reference numerals are used to designate substantially the same elements.

On the other hand, terms used herein are to be understood as described below. While such terms as "first" and "second," etc., may be used to describe various elements, such elements must not be limited to the above terms. The above terms are used only to distinguish one element from another. For example, a first element may be referred to as a second element, and likewise a second element may be referred to as a first element.

As used herein, the singular forms "a", "an" and "the" are intended to include the plural forms as well, unless the context clearly indicates otherwise. It will be further understood that the terms "include(s)", "including", "have (has)" and/or "having", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Respective steps of the methods described herein may be performed in a different order than that which is explicitly described. In other words, the respective steps may be performed in the same order as described, simultaneously, or in a reverse order.

FIG. 1 illustrates a rapid cell culture test device designed such that fluid films with a uniform thickness are formed according to one embodiment of the present disclosure. Referring to FIG. 1, the rapid cell culture test device 100 has an array structure of a plurality of aligned well units 110.

FIG. 2 schematically illustrates a well unit structure of a rapid cell culture test device designed such that fluid films with a uniform thickness are formed according to one embodiment of the present disclosure, when viewed in different directions: (a) plan view of the well unit when viewed from above, (b) and (c) enlarged perspective views of the bottom surface of the well unit, and (d) exploded view of the well unit when viewed from the right side.

Referring to FIG. 2, the well unit 110 includes a first sub-well 120 in which a first fluid is accommodated and a barrier structure 140 surrounding the first sub-well 120 to define the area of the first sub-well 120. The plurality of the aligned well units 110 may have overall dimensions similar to the wells of a commercial multi-well plate. Preferably, the centers of the well units 110 coincide with the centers of the wells of a commercial multi-well plate. The cell culture test device may further include second sub-wells 130 spatially separated from the first sub-wells to accommodate a second fluid.

Multi-well plates are standard tools for processing and analyzing a large number of samples in chemical, biochemical, and/or biological assays. Multi-well plates may take various forms, sizes, and shapes. Generally, multi-well plates are designed to have standard sizes and shapes and have standard arrangements of wells. For compatibility with such multi-well plates, the plurality of well units may have standard arrangements of wells, including those found in 96-well plates (12×8 array of wells), 384-well plates (24×16 array of wells), and 1536-well plates (48×32 array of wells). The arrangements of the plurality of well units may be identical or similar to those of various commercially available multi-well plates. The cell culture test device 100 is readily compatible with various conventional biological analysis techniques because its dimensions are similar to those of a commercial multi-well plate.

Each of the first and second fluids typically includes 70% to 99% by weight, preferably 85% to 99% by weight, most preferably 93% to 99% by weight of water as a dispersion medium or solvent. For example, the first fluid may be a mixture solution of a gelling agent-containing liquid medium and a biological agent. When the content of water in the first fluid is within the range defined above, the water can exhibit optimal performance as a dispersion medium.

A capillary channel 124 recessed from the bottom surface 122 of the first sub-well 120 while traversing the bottom surface 122 is formed to accommodate the first fluid.

The barrier structure 140 may be divided into at least two portions that have different inner wall heights so as to attract the first fluid to either side. Specifically, the barrier structure 140 is divided into a barrier portion A 140*a* located adjacent to one end 124*a* of the capillary channel 124 and a barrier portion B 140*b* located adjacent to the other end 124*b* of the capillary channel 124. The barrier portion A 140*a* is greater in height than the barrier portion B 140*b*. That is, the barrier portion A 140*a* and the barrier portion B 140*b* are asymmetric in height. The location of the barrier portion A 140*a* adjacent to one end of the capillary channel 124 or the location of the barrier portion B 140*b* adjacent to the other end of the capillary channel 124 means that the barrier portions may be located in direct contact with the corresponding ends of the capillary channel or may be separated from the corresponding ends of the capillary channel by a microchannel 126 formed therebetween.

Due to this height difference, a change in the level of the first fluid at the other end 124b of the capillary channel 124 depending on the amount of the first fluid dispensed is minimized when the barrier portion A 140a is wetted with the first fluid introduced into the first sub-well 120 along its inner wall.

FIG. 3 illustrates cross-sectional views of the well unit and a difference in the level of the fluid introduced into the well unit. The first sub-well 120 may be in the form of a well that has a sufficient space to accommodate the first fluid. The volume of the inner space of the well is not particularly limited but may be large enough to observe responses for a long time after introduction of the first fluid. The volume of the inner space of the well may be, for example, 1 μl to 50 μl. If the volume of the first sub-well is less than 1 μl, it is difficult to form a solid thin film having a size sufficient for observation. Meanwhile, if the volume of the first sub-well exceeds 50 μl, a large amount of a sample is required, resulting in a reduction in efficiency.

The capillary channel 124 is recessed in the depth direction with respect to the bottom surface 122 of the first sub-well 120 to accommodate a solid thin film formed by gelling the first fluid. When the recess has a depth d1 of about 0.1 to about 0.5 mm and a width w3 of about 0.1 to about 1 mm, it can retain the first fluid by capillary action. As a result, the dispensed first fluid is preferentially introduced into the capillary channel 124 rather than into other regions. Accordingly, the levels of the first fluid in the capillary channels can always be maintained constant although different amounts of the first fluid are dispensed into the well units, for example, smaller amounts of the first fluid are dispensed into some of the well units. If the dimensions of the capillary channel are out of the ranges defined above, the fluid may not maintain its constant level or may not spread well in the channel.

The role of the barrier structure depending on its shape will be described in more detail based on a comparison of (a) and (b) of FIG. 4. (a) of FIG. 4 illustrates a well structure of a conventional cell culture test device. Referring to (a) of FIG. 4, the level of the fluid varies depending on the amount of the fluid dispensed. When a reduced amount of the fluid is dispensed, the level h1 of the fluid is low. The level rises to h2 with increasing amount of the fluid dispensed. This level difference affects the diffusion distance of the second fluid after gelling of the first fluid, leading to a difference in the growth of a biological agent such as a bacterial strain.

Referring to (b) of FIG. 4, when the amount of the first fluid dispensed increases, the height h3 of the portion of the first fluid affected by capillary action is greatly changed but the height h4 of the interface of the first fluid in the capillary channel 124 where the behavior of the biological agent is observed is kept almost constant. Generally, a liquid in a container climbs slightly up the wall of the container at the edge of the liquid-container interface. This phenomenon is called capillary action. The basic principle is that intermolecular attraction between the liquid and the solid acts as a main force as the mass of the liquid decreases and gravity dominates the intermolecular attraction as the mass-to-surface area ratio of the liquid increases. Based on this principle, the present inventors have succeeded in designing a rapid cell culture test device in which a change in the height of a liquid-gas interface in a specific region is minimized. For example, the present inventors have applied this principle to a solid whose surface is hydrophilic above a predetermined level (contact angle<90°) for a water-based solution as well as a mixture of agarose and a bacterial solution dispensed.

Referring to an example where a mixture of agarose and a bacterial solution is dispensed into the well unit structure illustrated in FIG. 2, the agarose solution is evenly spread throughout the first sub-well 120 by the microchannel 126 and is stopped at the same height as the barrier portion B 140b of the barrier structure 140 but rises along the inner wall of the barrier portion A 140a to a level higher than the surroundings. Here, when the amount of the first fluid is small overall, the width of the capillary channel 124 is made smaller than that of the microchannel 126, which is preferable in terms of solution dispensing performance. For reference, when the amount of the first fluid is large overall, the excess solution is absorbed in the barrier portion A 140a of the barrier structure 140 so that elevation of the liquid-gas interface at one end 124a of the capillary channel can be minimized.

The bottom surface 122 may have a circular, elliptical or polygonal shape. As illustrated in FIGS. 2 and 3, the shape of the bottom surface 122 is close to a circle, like that of the well unit. The capillary channel 124 may extend across the bottom surface 122 such that its both ends face the barrier structure, with the result that when the first fluid is introduced while being in contact with the bottom surface 122 of the first sub-well 120, it can be retained in the capillary channel by capillary action regardless of its amount dispensed. That is, since the dispensed first fluid is preferentially introduced into the capillary channels 124 rather than into other regions, the levels of the first fluid in the capillary channels can always be maintained constant although different amounts of the first fluid are dispensed into the well units, for example, smaller amounts of the first fluid are dispensed into some of the well units. As used herein, the term "constant level" corresponds to the level of the fluid indicated by orange in the dotted rectangular box in (b) of FIG. 4. Unless otherwise specified, this term refers to the difference h4 between the height of the bottom surface 122 from the bottom of the well unit and the height of the lower end of the capillary channel 124 from the bottom of the well unit.

The bottom surface 122 has a width w1 in the range of 3.7 mm to 6 mm and the first sub-well 120 has a width in the range of 5 mm to 8 mm. The shape of the bottom surface is not particularly limited. The ratio of the width of the bottom surface 122 to the width of the first sub-well 120 is not particularly limited but is preferably in the range of 0.7:1 to 0.75:1. Within this range, a smooth flow of the introduced first fluid due to the microchannel is ensured, facilitating the formation of a solid thin film. If the ratio is out of the range defined above, a smooth flow of the fluid due to the microchannel is not ensured, failing to form a solid thin film.

At least one capillary channel 124 may be recessed from the bottom surface 122. The capillary channel 124 serves to well fix the first fluid to the bottom surface 122 by capillary action. The capillary channel 124 may have a circular or elliptical shape in cross section. Alternatively, the cross-sectional shape of the capillary channel 124 may be polygonal such as quadrangular, pentagonal or hexagonal.

One or more capillary channels 124 may be recessed from the bottom surface. In this case, the capillary channels 124 may be a plurality of microwells spaced apart from each other or may be in the form of microchannels. The capillary channel 124 may be, for example, in the form of a rectangular microchannel, as illustrated in FIG. 3 and (b) of FIG. 4. For example, the capillary channel 124 may have a width in the range of 100 μm to 1 mm and a depth (or thickness) in the range of 100 μm to 500 μm. These dimensions facilitate subsequent imaging and enable uniform spreading of the first fluid in the first sub-well 120 by capillary action. In addition, since the dispensed first fluid is preferentially introduced into the capillary channels 124 rather than into other regions, the levels of the first fluid in the capillary channels can always be maintained constant although different amounts of the first fluid are dispensed into the well units, for example, smaller amounts of the first fluid are dispensed into some of the well units. Furthermore, the first fluid can be well fixed in the capillary channels. The first fluid is dispensed in an amount of 1 μl to 50 μl, preferably 10 μl to 20 μl. The amount of the first fluid depends on the overall size of the solid structure. If the amount of the first fluid dispensed is less than the lower limit, the density of cells in the mixture solution is low, making it difficult to observe the cells. Meanwhile, if the amount of the first fluid dispensed exceeds the upper limit, the first fluid may not form a thin film whose height is maintained constant or may overflow from the barrier structure 140.

Preferably, the capillary channel has a shape for easy observation of cells. The first fluid may be a liquid medium containing a gelling agent. In this case, the first fluid is gelled after the lapse of a predetermined time, with the result that the first fluid filling the bottom surface 122 as well as the capillary channel 124 can form a solid thin film having a specific shape by surface tension against the inner wall of the reactor, as illustrated in (b) of FIG. 4. Particularly, the height of the solid thin film at a position for imaging (usually a position where the thin film has the lowest height) in the capillary channel 124 can be adjusted within the error range regardless of the amount of the first fluid. This is advantageous in that the degree of precision of the well can be sufficiently adjusted by the physical approach alone.

The ratio of the width w3 of the capillary channel 124 to the width w2 of the first sub-well 120 is 0.01:1 to 0.2:1, more preferably 0.1:1 to 0.12:1. If the ratio of the width of the capillary channel to the width of the first sub-well is <0.01:1, the volume of the capillary channel to accommodate the first fluid is small, making it difficult to observe cells. Meanwhile, if the ratio of the width of the capillary channel to the width of the first sub-well is >0.2:1, capillary action cannot take place appropriately.

Targets present in the first fluid can be observed through the bottom surface 122, specifically the capillary channel 124 recessed from the bottom surface. To this end, the bottom surface 122, specifically at least a portion of the capillary channel 124 recessed from the bottom surface, may be made of an optically transparent material. For example, the body of the cell culture test device may be made of a transparent material. Preferably, the transparent material is a suitable material for injection molding. Examples of more preferred transparent materials include polyethylene (PE), polypropylene (PP), polymethyl methacrylate (PMMA), cyclic olefin polymer (COP), polystyrene (PS), polycarbonate (PC), Teflon™, polyvinyl chloride (PVC), polybutylene terephthalate (PBT), polyethylene terephthalate (PET), and acrylonitrile-butadiene-styrene copolymer (ABS). Most preferably, the transparent material is polystyrene that is transparent enough to easily observe solid thin films.

Referring back to FIGS. 2 and 3, the cell culture test device may further include second sub-wells spatially separated from the first sub-wells to accommodate a second fluid and designed to load a bioactive agent in a solid form at specific locations thereof. Each of the second sub-wells may be in the form of a well with that has a sufficient space to accommodate a second fluid. The second sub-wells may include a bioactive agent in the form of a dried solid. In this case, the bioactive agent in the form of a solid can be dissolved in the second fluid introduced into the second sub-wells. As a result, a solution of the bioactive agent can be prepared.

The barrier structures 140 may define the first sub-wells 120 and may have a height sufficient to prevent the introduced first fluid from overflowing from the first sub-wells. The barrier structures are located between the first sub-wells and the second sub-wells to partition the individual sub-wells. The barrier structures 140 may have such a height that the first fluid introduced into the first sub-wells 120 does not overflow into the second sub-wells 130 to fill the bottom surfaces 122 as well as the capillary channels 124. The barrier structures 140 prevent the first fluid from overflowing into the second sub-wells to prevent the first fluid from contaminating the second sub-wells including the bioactive agent in a solid form. Since targets present in the first fluid come into contact with the bioactive agent after being gelled by the gelling agent present in the first fluid, the presence of the barrier structures enables sequential cell culture testing. At the same time, the barrier portion B 124b of the barrier structure 140 has such a height that the second fluid introduced into the second sub-well overflows into the first sub-well 120. Here, the barrier portion B 124b located adjacent to the other end of the capillary channel 124 has a height to allow the second fluid to overflow into the first sub-well 120.

The barrier portion A located adjacent to one end of the capillary channel 124 includes the inner wall edge of the first sub-well. The edge may be a single edge or a boundary where the two inner walls meet. The edge is not necessarily round but may be angled. Preferably, the inner wall of the barrier portion A 140a is hydrophilized using plasma or a surface treating solution (such as a surfactant) to create a capillary effect.

Referring back to FIG. 2, the microchannel 126 surrounds the bottom surface 122 along the circumference of the inner wall of the barrier structure 140 such that the first sub-well 120 is uniformly filled with the introduced first fluid. The microchannel 126 is preferably recessed deeper than the capillary channel 124 recessed from the bottom surface 122. This is effective in evenly spreading the solution.

FIG. 5 shows an antibiotic testing process using the cell culture test device.

Referring to FIG. 5, first, a liquid medium containing a gelling agent is mixed with a biological agent to prepare a mixture solution as a first fluid (see (a) of FIG. 5). The liquid medium may include at least about 95% of water and may be gelled in the presence of a gelling agent. For example, the gelling agent may be agar, agarose, gelatin, alginate, collagen or fibrin. The use of agar or agarose is preferred. For example, agar may be used in an amount of 0.3 to 4% by weight in the liquid medium. The liquid medium usually requires no nutrients. In some examples, however, the liquid medium may include nutrients. The liquid medium may be a solution including a medium stimulating the division of particular cells. If the agar content is less than 0.3% by weight, the liquid medium may not be gelled. Meanwhile, if the agar content exceeds 4% by weight, the liquid medium may be excessively gelled, making it difficult to diffuse the biological agent, and the sol-gel transition temperature is raised, possibly affecting cells.

Examples of suitable biological agents include viruses, bacteria, fungi, algae, protozoa, parasitic pathogens, human and mammalian cells, and biofilms. The biological agent may be a mixture of an infectious biological agent (e.g., a bacterial, viral or fungal strain) and blood cells. For example, the biological agent may be blood collected from a human infected with bacteria. In this case, a medium stimulating the division of only the bacterial cells can be used to distinguish the bacterial cells from the blood cells based on their different sizes. The biological agent may grow in a liquid or solid medium and the growth of the biological agent may be affected by the kind and concentration of a foreign bioactive agent. The density of the biological agent in the mixture solution is from $10^2$ to $10^{10}$ cells/ml, preferably from $10^4$ to $10^{10}$ cells/ml, more preferably from $10^5$ to $10^9$ cells/ml. If the density of the biological agent is below the lower limit, it may be difficult to perceive the location of the biological agent. Meanwhile, if the density of the biological agent exceeds the upper limit, it may be difficult to perceive the individual state of the biological agent.

Next, the mixture solution is introduced into the bottom surface 122 of the first sub-well, as shown in (b) of FIG. 5. The mixture solution may be introduced in an amount sufficient to cover the bottom surface 122 as well as the surface of the capillary channel 124 in the first sub-well. The volume of the mixture solution introduced into the bottom surface 122 of the first sub-well 110 is preferably 1 μl to 50 μl, more preferably 10 μl to 20 μl. If the volume of the mixture solution introduced is less than the lower limit, the density of cells in the mixture solution is low, making it difficult to observe the cells. Meanwhile, if the volume of the mixture solution introduced exceeds the upper limit, the mixture solution may not form a solid thin film whose height is maintained constant or may overflow from the barrier structure 140. The formation of the capillary channel 124 recessed from the bottom surface 122 of the first sub-well is effective in retaining the first fluid by the liquid-solid attraction to maintain the minimum height of a solid thin film over the entire area of the bottom surface as well as the capillary channel by capillary action. The capillary channel 124 also allows the mixture solution to be well fixed to the desired area. FIG. 6 shows loading of a sample into the first sub-well. Referring to FIG. 6, the sample is fixed to only the desired area in the well due to the formation of the capillary channel 124 and the microchannel 126. Specifically, the first fluid filling the bottom surface 122 as well as the capillary channel 124 can form a solid thin film having a specific shape by surface tension against the inner wall of the reactor (see the region represented in red in FIG. 6). Particularly, the height of the solid thin film at a position for imaging (usually a position where the thin film has the lowest height) in the capillary channel 124 can be adjusted within the error range regardless of the amount of the first fluid. This is advantageous in that the degree of precision of the well can be sufficiently adjusted by the physical approach alone.

As shown in (b) of FIG. 5, the biological agent of the mixture solution may be a mixture of an infectious biological agent (e.g., a bacterial strain) and blood cells. For example, the biological agent may be a culture of blood collected from a human infected with bacteria, i.e. a culture of blood positive for bacterial infection. In this case, a liquid medium stimulating the division of only the bacterial cells can be used to distinguish the bacterial cells from the blood cells based on their different sizes. The biological agent positive for bacterial infection may be collected and diluted with the gelling agent-containing liquid medium. Thus, there is no need to separate the bacteria from the blood sample, shortening the test time. Examples of media capable of stimulating the division of only bacterial cells include Mueller-Hinton broth (MHB), Mueller-Hinton agar (MHA), Luria-Bertani broth (LBB), and Luria-Bertani agar (LBA).

The mixture solution is gelled to form a solid thin film immobilized with the biological agent. When the temperature of the liquid medium drops, the medium is gelled, which restricts the mobility of the biological agent. This immobilization facilitates continuous observation of the motile biological agent.

The cell culture test device 100 or the bottom surface 122 is preferably made of a transparent material for optical imaging. Referring again to (b) of FIG. 5, the liquid medium is applied to the bottom surface 122 of the first sub-well of the cell culture test device and is gelled to form a solid thin film. The capillary channel 124 may extend across the bottom surface 122 such that its both ends face the barrier structure, with the result that when the first fluid is introduced while being in contact with the bottom surface 122 of the first sub-well 120, it can be retained in the capillary channel by capillary action regardless of its amount dispensed. That is, since the dispensed first fluid is preferentially introduced into the capillary channels 124 rather than into other regions, the levels of the first fluid in the capillary channels can always be maintained constant although different amounts of the first fluid are dispensed into the well units, for example, smaller amounts of the first fluid are dispensed into some of the well units. The constant level refers to the difference between the height h1 of the bottom surface 122 from the bottom of the well unit and the height h2 of the capillary channel 124 from the bottom of the well unit. The constant level may be in the range of 1 μm to 5 mm, 1 μm to 3 mm, 1 μm to 2 mm, 1 μm to 1.5 mm, 1 μm to 1 mm, 1 μm to 800 μm, 1 μm to 500 μm, 1 μm 100 μm, 10 μm to 3 mm, 100 μm to 500 μm, 10 μm to 1 mm, 100 μm to 1 mm, 200 μm to 1 mm, 500 μm to 1 mm or 100 μm to 500 μm. The constant level is preferably 100 μm to 500 μm. Due to the formation of the solid thin film whose thickness is constant in the range defined above, the biological agent immobilized into the solid thin film can be easily observed on a single cell or single cell colony basis.

The width of the capillary channel 124 is 100 μm to 1 mm when the size of an imaging area is taken into consideration. Preferably, the width of the capillary channel 124 is in the range of 0.5 mm to 1 mm. Within this range, the capillary channel 124 of the first sub-well can provide a space where cells are immobilized on the desired area. In addition, the entire region of the capillary channel can be observed because the dimensions of the capillary channel are not larger than those of an imaging system.

The shape and width of the capillary channel are not especially limited as long as the largest possible amount of the mixture solution (including the gelling agent-containing liquid medium and the biological agent) can be introduced while maintaining the dimensions and width, which facilitates accurate control over responses to the bioactive agent. It is desirable that the dimensions of the capillary channel are not larger than those of an imaging system, because the entire region of the capillary channel can be observed without the need to move the cell culture test device.

The thickness and width of the solid thin film may vary depending on where they are measured. However, the thickness of the solid thin film to be substantially observed is determined depending on the depth and width of the capillary channel because targets are observed through the capillary channel. As used herein, the term "thin film" refers to a thin layer that has a thickness sufficient to immobilize the biological agent and to observe single cells or single cells colonies. The thickness of the thin film is typically in the range of 1 μm to 5 mm, 1 μm to 3 mm, 1 μm to 2 mm, 1 μm to 1.5 mm, 1 μm to 1 mm, 1 μm to 800 μm, 1 μm to 500 μm, 1 μm to 100 μm, 10 μm to 3 mm, 100 μm to 500 μm, 10 μm to 1 mm, 100 μm to 1 mm, 200 μm to 1 mm or 500 μm to 1 mm, but is not particularly limited to this range. The thickness of the solid thin film may correspond to the size of a side of the solid thin film in a direction perpendicular to a side of the solid thin film to be observed. Within the thickness range of the solid thin film defined above, the biological agent immobilized in the solid thin film can be observed on a single cell or single cell colony basis.

Focus marks may be provided on the undersides of the first sub-wells to provide information on the positions of targets. FIG. 7 shows focus marks provided on the undersides of the first sub-wells. Referring to FIG. 7, the focus marks may be marked on the undersides of the first sub-wells such that target areas of the cell culture test device are automatically tracked. The focus marks are provided in the form of microchannels by injection molding. Since the biological agent is immobilized in the solid thin films, the use of the focus marks enables imaging of the same areas every time pictures are taken. The focus marks serve to correct the positions of targets in the three axial directions, i.e. x-, y-, and z-axis directions, in the automatic tracking of target areas.

As shown in (c) of FIG. 5, a second fluid containing a bioactive agent is provided to the well unit 110 or a solvent capable of dissolving a dried bioactive agent may be provided to the well unit 10 loaded with the bioactive agent. Alternatively, a second fluid may be directly provided to the first sub-well in the well unit 110. A second sub-well including a bioactive agent in a solid form is provided with a solvent capable of dissolving the bioactive agent. When a bioactive agent is absent in the second sub-well, a solution containing a bioactive agent can be provided to the second sub-well. Herein, the bioactive agent may include a substance selected from antibiotics, anticancer agents, drugs such as immunosuppressants, nutrients, cellular secretions, neurotransmitters, viruses, cells, micro RNAs, proteins, antigens, antibodies, and DNAs. The second sub-well may include a bioactive agent in a dried solid form. The solvent capable of dissolving the dried bioactive agent may be selected from water, cell culture media, dimethylformamide (DMF), and dimethyl sulfoxide (DMSO). The solvent may be introduced by pipetting such that the solid bioactive agent is completely dissolved and the resulting solution has a uniform concentration. Any drying process that does not deteriorate the efficacy of the bioactive agent may be used without limitation to dry the bioactive agent. The bioactive agent is preferably dried by heat drying, freeze drying or vacuum drying, most preferably heat drying. The bioactive agent thus dried is introduced into the well unit 110. Alternatively, the bioactive agent may be introduced into the well unit 110 and dried by the drying process mentioned above. A bioactive agent may also be introduced into the first sub-well and dried. However, it is preferable to introduce a dried bioactive agent into the second sub-well or to introduce a bioactive agent into the second sub-well and dry the bioactive agent.

As shown in (c) of FIG. 5, the solvent capable of dissolving the bioactive agent is provided in such an amount that it crosses over the barrier portion 140*b* of the barrier structure 140, to allow the bioactive agent to diffuse into the solid thin film in the first sub-well 120. Also when the bioactive agent is absent in the second sub-well 130, the solution containing the bioactive agent is provided in such an amount that it crosses over the barrier portion 140*b* of the barrier structure 140, to allow the bioactive agent to diffuse into the solid thin film in the first sub-well 120. The volume of the solution containing the bioactive agent or the solvent capable of dissolving the bioactive agent introduced into the second sub-well 130 is not limited as long as the solution containing the bioactive agent crosses over the barrier portion 140*b* of the barrier structure 140 to form an interface with the solid thin film formed in the first sub-well 120. The volume is preferably 11 μl to 350 μl, more preferably from 80 μl to 100 μl. If the second sub-well has a volume of less than 11 μl, the reduced size of the well may make pipetting and drying difficult. Meanwhile, if the second sub-well has a volume exceeding 350 μl, large amounts of a sample and reagents are required, resulting in a reduction in efficiency.

Next, as shown in (d) of FIG. 4, responses of the biological agent to the bioactive agent are observed. The bioactive agent-containing solution diffuses into the solid thin film through the interface with the solid thin film and meets the biological agent immobilized in the solid thin film. The biological agent immobilized in the solid thin film is widely distributed in the horizontal direction with respect to the observation direction, and as a result, the biological agent can be observed on a single cell or single cell colony basis. According to the testing method of the present disclosure, changes in the growth of single bacteria can be generally observed within several tens of minutes (normally 30 minutes) and those of single colonies of bacteria can be typically observed within 4 to 6 hours. Accordingly, the testing method of the present disclosure allows for the identification of the effect of the bioactive agent on the biological agent in a more accurate and rapid manner than conventional testing methods. For example, when the bioactivity of the bioactive agent on bacterial cells is tested, the test can be completed within 3 to 4 hours. The testing method of the present disclosure can be used to observe changes in the morphology of single cells or changes of single cell colonies in the presence of various antibiotics by time-lapse imaging.

Responses of the biological agent to the bioactive agent can be observed on a single cell colony basis to determine the minimum inhibitory concentration (MIC) or minimum biofilm eradication concentration (MBEC) of the bioactive agent. The cell culture test device of the present disclosure is very useful for biofilm assay as well as antibiotic susceptibility testing. Biofilms are found in areas infected with microbes or to which microbes are attached. Biofilms refer to films that constitute mucilaginous microbial complexes, which are formed by microbes surrounded by polymer matrices. The formation of biofilms can greatly affect human health. Biofilms cause pulmonary infections, otitis media, periodontitis, and other infectious diseases. The resistance of bacteria present in biofilms to antibiotics is at least 1,000 times stronger than that of suspended bacteria. Flow cell systems and well-based systems have been used to investigate biofilms. However, these assay systems require a long time of several days for biofilm formation. Other difficulties associated with the use of the assay systems are that biofilms need to be stained and confocal microscopes should be used for observation. Further experiments are needed for the measurement of minimum inhibitory concentration (MIC) or minimum biofilm eradication concentration (MBEC). Such systems are very large in size and they fail to clearly show biofilm formation stages and to represent in vivo biofilm formation.

Thus, there is a need for efficient systems that are suitable to investigate the formation of biofilms and the reactivity of biofilms with antibiotics. In consideration of this need, the cell culture test device according to one embodiment of the present disclosure proves to be an excellent alternative to conventional test devices.

An optical measurement system may be used for observation. The optical measurement system may include an imaging system such as a CCD or CMOS camera. The optical measurement system may include optical units or devices necessary for focusing and light imaging such as a lens, an illuminator, and a light guide. The optical measurement system may include an image processing system for processing and analyzing image data observed by the imaging system. The optical measurement system rapidly records and analyzes changes in the growth of the biological agent observed during testing to obtain test results. The central portion of the first sub-well where the gelled first fluid forms an interface with the second fluid becomes an imaging area. The imaging area may have a size of about 400 µm×800 µm to about 800 µm×1600 µm.

Consequently, the use of the testing method based on the immobilization of the biological agent and the diffusion of the bioactive agent can greatly reduce the amounts of drugs and cells necessary for drug testing, and enables rapid tracking of changes in the growth of single cells or single cell colonies to obtain test results on the drugs as rapidly as 2 hours (normally within 6 hours), compared to the prior art. This is the most rapid testing speed known thus far.

The rapid cell culture test device of the present disclosure may be designed to be openable and closable through a fastening structure or may be provided with a cover film made of silicone, polyethylene terephthalate (PET), polyethylene (PE), polypropylene (PP), polystyrene (PS), polycarbonate (PC), Teflon™ or polyvinyl chloride (PVC). A cruciform or X-shaped punch may be formed at a position of the cover film corresponding to the underlying first sub-well 120. The punch can serve as an inlet portion through which a slight amount of the first fluid is easily introduced. A cruciform or X-shaped punch may be formed at a position of the cover film corresponding to the underlying second sub-well 130. The punch can serve as an inlet portion through which the second fluid is easily introduced. In terms of convenience of use, it is preferable that the shape of the inlet portion through which the first fluid is introduced is different from that of the inlet portion through which the second fluid is introduced.

The present disclosure will be explained in more detail with reference to the following examples. However, these examples are not intended to limit the spirit of the disclosure.

EXAMPLE 1

A thermoplastic resin (polystyrene (PS)) was injection molded into the multi-well-based cell culture test device illustrated in FIG. 1, which had an array of 12×8 aligned well units. After injection molding, the inner walls of the cell culture test device were hydrophilized.

Agarose containing microbeads was mixed with a bacterial solution (agarose: bacterial solution=50:1) to prepare a first fluid. The first fluid was dispensed into the well units. The agarose solution was evenly spread throughout the first sub-wells 120 by the microchannels 126. The agarose solution was stopped at the same height as the barrier portions B 140b of the barrier structures 140 but rose along the inner walls of the barrier portions A 104a of the barrier structures 140 to a level higher than the surroundings. When the amount of the first fluid was small overall, the width of the capillary channels 124 was made smaller than that of the microchannels 126d, which is preferable in terms of solution securing performance. For reference, when the amount of the first fluid was large overall, the excess solution was absorbed in the barrier portions A 140a of the barrier structures 140 so that elevation of the liquid-gas interface at one end 124a of each of the capillary channels was minimized.

COMPARATIVE EXAMPLE 1

The procedure of Example 1 was repeated except that a conventional microwell-based test system was used instead of the multi-well-based cell culture test device (see (a) of FIG. 4).

TEST EXAMPLE 1

The heights of the interfaces in the test devices used in Example 1 and Comparative Example 1 were measured. To this end, imaging was performed in the height direction. The first position where the beads were focused was designated as the bottom surface and the final position where all microbeads were defocused during the z-direction imaging was designated as the location of the thin film interface. The difference between the bottom surface and the thin film interface was defined as the height. The first fluid was dispensed in the amounts shown in FIG. 9. The resulting heights were plotted against the amounts of the first fluid ((a) of FIG. 9 for Comparative Example 1 and (b) of FIG. 9 for Example 1). The height of the solid thin film measured at the imaging position (corresponding to (d) of FIG. 5) was recorded as a function of the amount of the first fluid dispensed. The results are also shown in FIG. 9.

As shown in (a) of FIG. 9, the calculated slope (height deviation) in Comparative Example 1 was 65.069, with the lowest average height of 420.15. As shown in (b) of FIG. 9, the calculated slope (height deviation) in Example 1 was 15.37, with the lowest average height of 290.41.

These results concluded that the lowest height in Example 1 can be maintained lower than that in Comparative Example 1 and the variation in the height of the interface in Example 1 can be minimized despite the varying amounts of the first fluid introduced.

EXAMPLE 2

FIG. 10 shows growth of reference strain *E. coli* ATCC 25922 without antibiotics, which was observed at regular time intervals using the cell culture test device of the present disclosure. The bacterial colonies increased in size with time. The colonies of the strain were visible to the naked eye from 4 h after initiation of colonization.

FIG. 11 shows a process for susceptibility testing of reference strain *E. coli* ATCC 25922 to imipenem as an antibiotic, which was observed at regular time intervals using the cell culture test device of the present disclosure. The antibiotic was used at concentrations of 0.12 µg/ml to 2.0 µg/ml recommended by the Clinical & Laboratory Standards Institute (CLSI). The results were recorded at 2 h intervals until 6 h after initiation of testing. The minimum inhibitory concentration (MIC) of the antibiotic, an important factor in antibiotic susceptibility testing, could be determined, as shown in FIG. 11.

FIG. 12 shows a process for susceptibility testing of reference strain *S. aureus* ATCC 29213 to penicillin as an antibiotic, which was observed at regular time intervals using the cell culture test device of the present disclosure.

Colonies of *S. aureus* ATCC 29213 began to be observed in the presence of 0.25 μg/ml penicillin from 2 h after initiation of testing. The colonies increased in size and were made clear at 6 h after initiation of testing. Colonies were observed later in the presence of 0.5 μg/ml penicillin than in the presence of 0.25 μg/ml penicillin. Clear colonies were observed 6 h after initiation of testing. The MIC of the antibiotic against *S. aureus* ATCC 29213 was found to be 1.0 μg/ml.

FIG. 13 shows a process for susceptibility testing of reference strain *P. aeruginosa* ATCC 27853 to aztreonam as an antibiotic, which was observed at regular time intervals using the cell culture test device of the present disclosure. Colonies of *P. aeruginosa* ATCC 27853 were clearly observed in the presence of 1.0 and 2.0 μg/ml aztreonam 6 h after initiation of testing. Smaller colonies were observed even in the presence of 4.0 μg/ml aztreonam 6 h after initiation of testing. The MIC of the antibiotic against *P. aeruginosa* ATCC 27853 was found to be 8.0 μg/ml.

FIG. 14 shows a process for susceptibility testing of reference strain *E. faecalis* ATCC 29212 to gentamicin as an antibiotic, which was observed at regular time intervals using the cell culture test device of the present disclosure. Small but clear colonies of the strain were observed in the presence of 4.0 μg/ml gentamicin 6 h after initiation of testing. The MIC of the antibiotic against *E. faecalis* ATCC 29212 was found to be 8.0 μg/ml.

FIG. 15 shows the results of susceptibility testing of Gram-negative strains *Enterobacter cloacae, Klebsiella pneumoniae, Pseudomonas aeruginosa*, and *Acinetobacter baumannii* obtained from four blood samples to antibiotics, which was observed using the cell culture test device ("DRAST") of the present disclosure. The tests were conducted on various drugs that are currently used in testing organizations. A conventional testing method based on broth microdilution (BMD) and the testing method using the cell culture test device of the present disclosure were used to test the susceptibility of the strains to the antibiotics, and the results were compared. *E. cloacae* was intermediate resistance (I) to ciprofloxacin in the BMD testing method and showed a susceptible (S) to ciprofloxacin in the testing method using the cell culture test device (DRAST) of the present disclosure. *E. cloacae* showed a resistance (R) to ertapenem in the BMD testing method and showed an intermediate resistance (I) to ertapenem in the testing method using the cell culture test device of the present disclosure. The strains showed different responses (i.e. susceptibility (S) vs. intermediate resistance (I) or intermediate resistance (I) vs. resistance (R)) to the above-mentioned antibiotics in the BMD testing method and the testing method using the cell culture test device of the present disclosure. Accordingly, these test results are all classified as minor errors of the first step judgement. The test results on the other drugs in the BMD testing method were in good agreement with those in the testing method using the cell culture test device of the present disclosure.

The minimum inhibitory concentrations (MICs) of all antibiotics against *P. aeruginosa*, *K. pneumoniae*, and *A. baumannii* determined in the BMD testing method were found to be slightly different from those determined in the testing method using the cell culture test device of the present disclosure, but the test results for susceptibility and resistance in the BMD testing method were in good agreement with those in the testing method using the cell culture test device of the present disclosure. The concentrations shown in FIG. 15 are expressed in μg/mL.

FIG. 16 shows the results of susceptibility testing of Gram-positive strains *Staphylococcus aureus, Staphylococcus epidermidis, Enterococcus faecalis*, and *Enterococcus faecium* obtained from four blood samples to antibiotics, which was observed using the cell culture test device ("DRAST") of the present disclosure. The tests were conducted on various drugs that are currently used in testing organizations. A conventional testing method based on broth microdilution (BMD) and the testing method using the cell culture test device of the present disclosure were used to test the susceptibility of the strains to the antibiotics, and the results were compared. *Staphylococcus aureus, Staphylococcus epidermidis, Enterococcus faecalis*, and *Enterococcus faecium* were detected in four blood samples. The test results on *S. aureus* and *S. epidermidis* in the BMD testing method were in good agreement with those in the testing method using the cell culture test device (DRAST) of the present disclosure.

*E. faecium* isolated from another sample showed a resistance (R) to linezolid in the BMD testing method and showed an intermediate resistance (I) to linezolid the testing method using the cell culture test device (DRAST) of the present disclosure. The strain showed different responses (i.e. intermediate resistance (I) vs. resistance (R)) to the above-mentioned antibiotics in the BMD testing method and the testing method using the cell culture test device of the present disclosure. Accordingly, these test results are all classified as minor errors of the first step judgement. The minimum inhibitory concentrations (MICs) of the antibiotics against *E. faecalis* determined in the BMD testing method were found to be different from those determined in the testing method using the cell culture test device of the present disclosure, but the test results for susceptibility and resistance in the BMD testing method were in good agreement with those in the testing method using the cell culture test device of the present disclosure. The concentrations shown in FIG. 16 are expressed in μg/mL.

Therefore, the cell culture test device of the present disclosure is very economical because its use can reduce the time for analysis, researchers' efforts, the amount of bioactive agents, the amount of media, and the number of plates.

Although the present disclosure has been described in detail with reference to the drawings and embodiments, those skilled in the art will appreciate that various variations and modifications can be made to the embodiments without departing from the spirit of the present disclosure as disclosed in the appended claims.

The invention claimed is:

1. A multi-well-based rapid cell culture test device designed such that fluid films with a uniform thickness are formed,
   the multi-well-based rapid cell culture test device comprises an array structure of a plurality of aligned well units,
   wherein,
   each of the plurality of aligned well units comprises a first sub-well in which a first fluid is accommodated and a barrier structure surrounding the first sub-well to define the area of the first sub-well,
   a capillary channel recessed from the bottom surface of the first sub-well while traversing the bottom surface is formed to accommodate the first fluid,
   the barrier structure is divided into a barrier portion A located adjacent to one end of the capillary channel and a barrier portion B located adjacent to the other end of the capillary channel, and the barrier portion A being greater in height than the barrier portion B such that when the barrier portion A is wetted with the first fluid introduced into the first sub-well along its inner wall, a change in the level of the first fluid at the other end of the capillary channel depending on the amount of the first fluid dispensed is minimized.

2. The multi-well-based rapid cell culture test device according to claim 1, further comprising microchannels, each of which is formed surrounding the corresponding bottom surface along the circumference of the inner wall of the barrier structure to allow the introduced first fluid to uniformly fill the first sub-well.

3. The multi-well-based rapid cell culture test device according to claim 2, wherein the microchannel is recessed deeper than the capillary channel recessed from the bottom surface.

4. The multi-well-based rapid cell culture test device according to claim 1, wherein the inner wall of the barrier portion A is hydrophilized.

5. The multi-well-based rapid cell culture test device according to claim 1, wherein the barrier portion A located adjacent to one end of the capillary channel comprises an edge of the inner wall of the first sub-well.

6. The multi-well-based rapid cell culture test device according to claim 1, wherein at least a portion of the bottom surface is made of an optically transparent material such that targets present in the first fluid are observable through the bottom surface.

7. The multi-well-based rapid cell culture test device according to claim 1, further comprising second sub-wells spatially separated from the first sub-wells to accommodate a second fluid and designed to load a bioactive agent in a solid form at specific locations thereof.

8. The multi-well-based rapid cell culture test device according to claim 1, wherein the first fluid is a mixture solution of a gelling agent-containing liquid medium and a biological agent, and a second fluid is a solution containing a bioactive agent or comprises a solvent capable of dissolving a bioactive agent in a solid form.

9. The multi-well-based rapid cell culture test device according to claim 1, wherein the multi-well-based cell culture test device comprises polyethylene (PE), polypropylene (PP), polymethyl methacrylate (PMMA), cyclic olefin polymer (COP), polystyrene (PS), polycarbonate (PC), polytetrafluoroethylene (PFE), perfluoroalkoxy alkane (PFA), fluorinated ethylene propylene (FEP), polyvinyl chloride (PVC), polybutylene terephthalate (PBT), polyethylene terephthalate (PET) or acrylonitrile-butadiene-styrene copolymer (ABS) and is provided with a cover film made of silicone, polyethylene terephthalate (PET), polyethylene (PE), polypropylene (PP), polystyrene (PS), polycarbonate (PC), polytetrafluoroethylene (PFE), perfluoroalkoxy alkane (PFA), fluorinated ethylene propylene (FEP), or polyvinyl chloride (PVC).

10. The multi-well-based rapid cell culture test device according to claim 9, wherein the cover film has cruciform or X-shaped punches formed at positions corresponding to the sub-wells of the well units constituting the multi-well-based cell culture test device and serving as inlets through which the first fluid is introduced and inlets through which a second fluid is introduced.

11. A cell analysis method using a multi-well-based cell culture test device,
wherein,
the multi-well-based cell culture test device comprises an array structure of a plurality of aligned well units,
each of the plurality of aligned well units comprises a first sub-well in which a first fluid is accommodated and a barrier structure surrounding the first sub-well to define the area of the first sub-well,
a capillary channel recessed from the bottom surface of the first sub-well while traversing the bottom surface is formed to accommodate the first fluid,
the barrier structure is divided into a barrier portion A located adjacent to one end of the capillary channel and a barrier portion B located adjacent to the other end of the capillary channel, and
the barrier portion A being greater in height than the barrier portion B such that when the barrier portion A is wetted with the first fluid introduced into the first sub-well along its inner wall, a change in the level of the first fluid at the other end of the capillary channel depending on the amount of the first fluid dispensed is minimized,
the method comprises:
(a) providing a mixture solution of a gelling agent-containing liquid medium and a biological agent to the capillary channel recessed from the bottom surface of the first sub-well,
(b) gelling the mixture solution to form a solid thin film that is immobilized with the biological agent and minimizes elevation of the liquid-gas interface,
(c) providing a solution containing a bioactive agent to a second sub-well or providing a solvent capable of dissolving a bioactive agent in a solid form to a second sub-well loaded with the bioactive agent,
(d) introducing the bioactive agent-containing solution or the solvent capable of dissolving the bioactive agent in such an amount that the solution or the solvent crosses over the barrier, to allow the bioactive agent to diffuse into the solid thin film in the first sub-well, and
(e) observing responses of the biological agent to the bioactive agent.

12. The cell analysis method according to claim 11, further comprising (f) observing changes of the biological agent responding to the bioactive agent on a single cell colony basis to determine the minimum inhibitory concentration (MIC) or minimum biofilm eradication concentration (MBEC) of the bioactive agent.

* * * * *